(12) United States Patent
De Vries

(10) Patent No.: US 6,623,163 B2
(45) Date of Patent: Sep. 23, 2003

(54) MEDICAL C-ARM DEVICE PROVIDED WITH AN IMPROVED BEARING BLOCK

(75) Inventor: Hendrik Wijbe Johannes De Vries, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/071,383

(22) Filed: Feb. 8, 2002

(65) Prior Publication Data

US 2002/0150314 A1 Oct. 17, 2002

(30) Foreign Application Priority Data

Feb. 13, 2001 (EP) .............................. 01200501

(51) Int. Cl.⁷ .............................. F16C 29/04
(52) U.S. Cl. .......................... 384/58; 384/55
(58) Field of Search .............. 384/58, 51, 50, 384/59, 55

(56) References Cited

U.S. PATENT DOCUMENTS 4,737,039 A * 4/1988 Sekerich ...................... 384/18
4,798,149 A * 1/1989 Hoffmann ..................... 384/58

FOREIGN PATENT DOCUMENTS

DE          19824205       8/1999       .......... F16C/29/04

* cited by examiner

*Primary Examiner*—Lenard A Footland
(74) *Attorney, Agent, or Firm*—John Vodopia

(57) ABSTRACT

The invention relates to a device that is provided with a C-arm 7 for carrying medical devices 5, 6, which C-arm is adjustably attached to a carrier 4. The carrier is provided with a bearing block 11 that is provided with at least one row of roller elements 8 on both sides. The C-arm is constructed so as to be hollow and is provided on both sides with at least two oppositely situated running surfaces 15, 16 for the roller elements. The device is characterized in that a plurality of roller elements of one row is interconnected by means of an interconnecting member 9.

The invention also relates to a bearing block of the described kind that forms part of the device in accordance with the invention.

10 Claims, 2 Drawing Sheets

MEDICAL C-ARM DEVICE PROVIDED WITH AN IMPROVED BEARING BLOCK

The invention relates to a device that is provided with a C-arm for the mounting of medical equipment, which C-arm is attached to a carrier so as to be adjustable along its circumference, said carrier being provided with a bearing block that is provided with at least one row of roller elements on both sides, the C-arm being constructed so as to be hollow and being provided on both sides with at least two oppositely situated internal running surfaces for the roller elements.

Devices of the kind set forth are used in practice for medical examination of a patient. To this end, an emitter of, for example, X-rays is attached to one end of the C-arm whereas a corresponding receiver is attached to the opposite end. The C-arm is adjustable inter alia along its circumference and hence can be accurately positioned relative to the patient who is accommodated on a table, for example, during a surgical intervention.

In order to ensure safe operation in all circumstances, the design of a device of this kind should satisfy a number of design requirements that are contradictory in some respects. First of all, the beam from the emitter to the receiver should remain within predetermined boundaries in all circumstances. This means that the C-arm should have a high bending strength. Furthermore, the construction of the device should be as light as possible so as to achieve an as high as possible degree of moeuvrability. This is of importance, for example, for the displacement of the device and for the manual adjustment of the C-arm. Moreover, the device should be capable of withstanding large temperature differences as they may occur, for example, during transport.

In order to satisfy the described requirements, the operation of the bearing system for the C-arm should be light and smooth in combination with a minimum amount of play.

A device of the kind set forth is known from DE 198 24 205. The cited document describes a device for medical applications that is provided with a C-arm on which an X-ray source is mounted at one side while a corresponding receiver is mounted at the other side. The C-arm is mounted so as to be journaled on a carrier. The bearing block is provided on both sides with a row of eight wheels. Oppositely situated wheels are coupled in a two by two fashion by way of a common rotary shaft.

The known device has the drawback that its wheels have a limited service life only. It has been found that notably the outer wheels are subject to accelerated wear that is due to the rigid connection of the wheels to the bearing block.

It is an object of the present invention to provide a device of the kind set forth in which the described drawback is eliminated.

To this end, the device in accordance with the invention is characterized in that a number of the roller elements of one row is interconnected by way of a connection member. The device in accordance with the invention offers the advantage that the forces are more uniformly distributed among the roller elements. Consequently, the individual roller elements are more uniformly subject to wear and the service life of the bearing block as a whole is prolonged. Moreover, it is likely that a smaller number of roller elements will suffice for each row. For example, it might be feasible to use six roller elements for each row. Alternatively, materials of lower quality can be employed so that the cost of the device is reduced in any case.

The roller elements of one row in a first preferred embodiment are grouped in two or more sets of roller elements, each set of roller elements being interconnected by way of a connection member. Each set of roller elements may comprise two or more roller elements. This embodiment represents an elegant implementation of the invention that utilizes few mechanical parts only.

The roller elements of one row are preferably interconnected in pairs by way of connection members. Laboratory tests have shown that this embodiment very successfully passes a test in respect of service life.

Oppositely situated sets of roller elements in a further version of the first preferred embodiment are connected in pairs to a common rotary shaft on both sides of the bearing block. The number of mechanical parts is thus further reduced.

The connection members of two neighboring sets of roller elements in one row in an alternative version of the first preferred embodiment are interconnected by way of a further connection member. Preferably, oppositely situated further connection members are connected in pairs to a common rotary shaft on both sides of the bearing block.

Each connection member in a further preferred embodiment is movable mainly in the plane of the C-arm. In this embodiment irregularities in the bearing surfaces are taken up better. Irregularities of this kind occur inter alia because in given positions the C-arm exhibits some degree of bending, that is, within predetermined limits; consequently, such irregularities are intrinsic to normal use of the device.

The bearing block in another embodiment yet exhibits a curvature that corresponds to the curvature of the C-arm and the rotary shafts are provided along the curvature. The C-arm can thus be smoothly moved along the bearing block so as to be adjusted to the desired position.

The bearing block in another embodiment is provided with a number of side roller elements whose rotary shafts extend mainly perpendicularly to the rotary shafts of the roller members and the C-arm is provided with a third running surface for the side roller elements. The C-arm is now suitably supported in the lateral direction during its movement along its circumference, so that undesirable pivoting movements in the lateral direction are effectively taken up.

The invention also relates to a bearing block as described as part of the device in accordance with the invention.

The invention will be described in detail hereinafter with reference to the drawings; therein:

Figure 1:
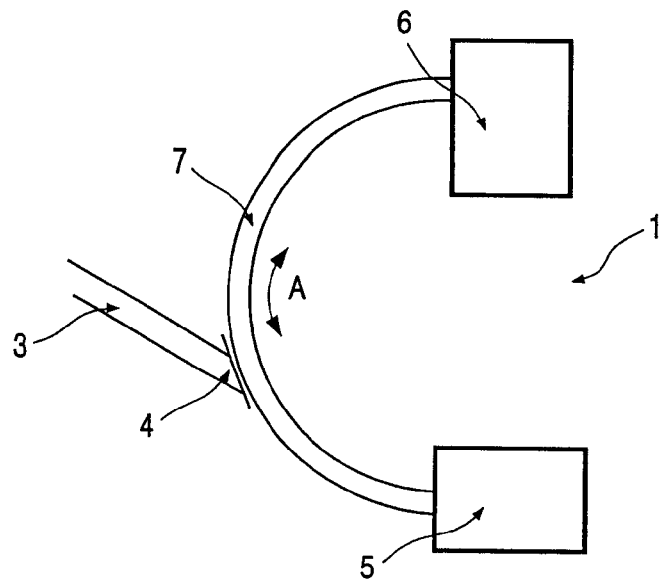
FIG. 1 is a diagrammatic view of a device for medical applications in which the invention is used.

FIG. 1 shows a device 1 for medical applications in which the invention is used. The device 1 is a so-called medical C-arm system. The C-arm 7 is attached to a carrier 3 by way of a bearing 4. Medical equipment is attached to both ends of the C-arm 7. In the present example the device 1 is an X-ray system that includes an X-ray source or emitter 5 and an oppositely situated image intensifier or receiver 6.

In practice the device 1 is used for performing examinations on a patient. The device 1 may be constructed so as to be mobile; to this end it is moeuvered in such a manner that the patient is positioned between the X-ray source 5 and the associated image receiver 6 during the examination. Various adjustment facilities are provided for adjusting the C-arm to the correct position. The C-arm 7 is movable inter alia along its circumference as indicated by way of the arrow A. The present invention relates to the bearing 4 that makes such movement possible.

Figure 2:
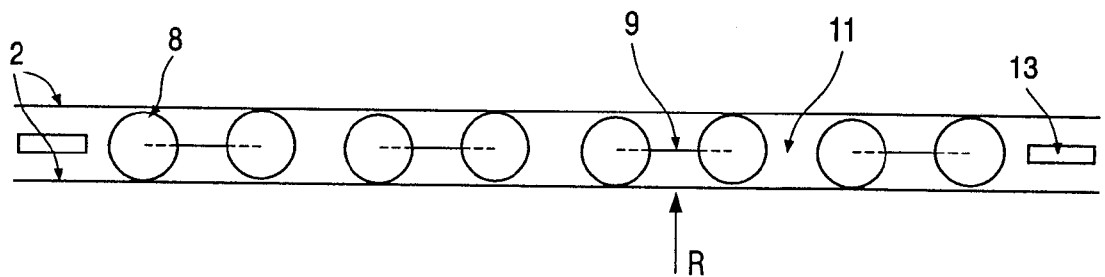
FIG. 2 is a diagrammatic, partly exposed side elevation of a first preferred embodiment of a bearing block in accordance with the invention.

FIG. 2 is a diagrammatic, partly exposed side elevation of a first preferred embodiment of the bearing block 11 of the bearing 4. It is to be noted that for the sake of simplicity the bearing block is shown so as to be straight, that is, with an infinite radius R. In practice, however, the bearing block preferably exhibits a curvature that corresponds to the curvature of the C-arm.

On both sides of the bearing block 11 there is provided one row of roller elements 8 that comprises eight elements in the present example. The roller elements 8 of one row in the preferred embodiment shown are interconnected in pairs by way of connection members 9.

Figure 3:
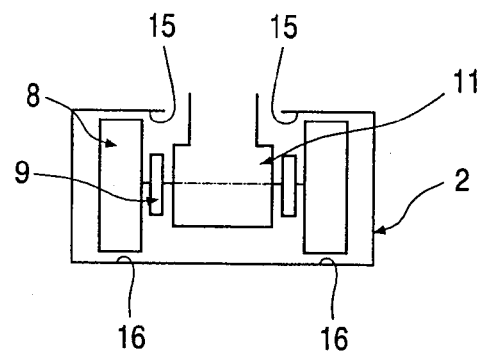
FIG. 3 is a diagrammatic cross-sectional view, taken at the area of the bearing in FIG. 1.

FIG. 3 is a diagrammatic cross-sectional view taken at the area of the bearing 4 in FIG. 1. It is clearly shown that the C-arm 2 is constructed so as to be hollow and that it has a generally U-shaped cross-section; on both sides thereof there are provided oppositely situated running surfaces 15 and 16. As is well known in this technical field, the distance between the running surfaces 15 and 16 is slightly larger than the diameter of the roller elements (also referred to as runners or wheels), so that the roller elements 8 will always be in contact with one of the running surfaces 15 or 16 during the movement of the C-arm.

Figure 4:
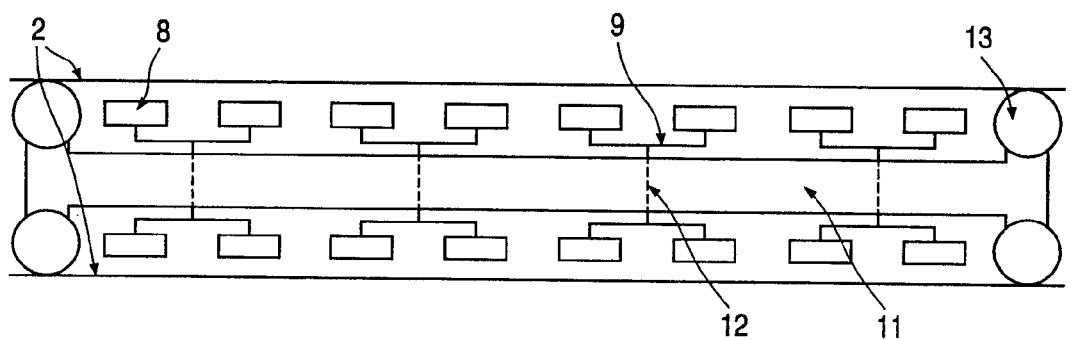
FIG. 4 is a diagrammatic longitudinal sectional view from above of the bearing of FIG. 3.

FIG. 4 is a diagrammatic cross-sectional view from above of the bearing 4 that is shown in FIG. 3. It is clearly shown that oppositely situated pairs of roller elements 8 are attached to a common rotary shaft 12. The connection members 9 are preferably connected to each rotary shaft 12 so as to be movable independently of one another. As is known in this technical field, side roller elements 13 are also connected to the bearing block 11. The side roller elements 13 serve to prevent undesirable lateral movement of the C-arm 2.

Figure 5:
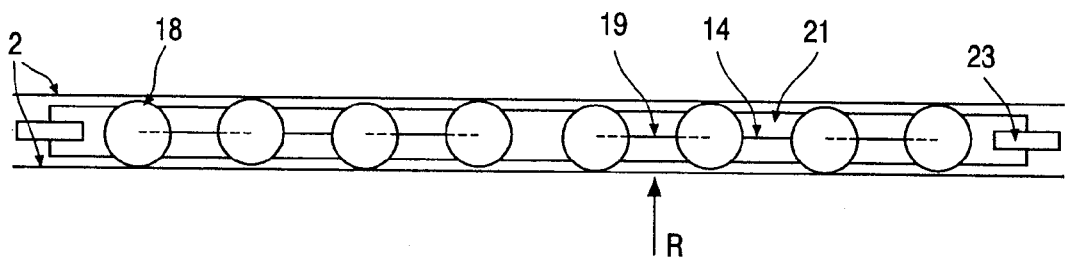
FIG. 5 is a diagrammatic, partly exposed side elevation of a second preferred embodiment of a bearing block in accordance with the invention.

FIG. 5 shows an alternative preferred embodiment of the bearing block in accordance with the invention. The Figure is a diagrammatic, partly exposed side elevation of the C-arm 2 with a bearing block 21 that is provided on both sides with roller elements 18 that are interconnected in pairs by way of connection members 19. Like in the previously described preferred embodiment, side roller elements 23 that are known per se are mounted on the bearing block 21.

Figure 6:
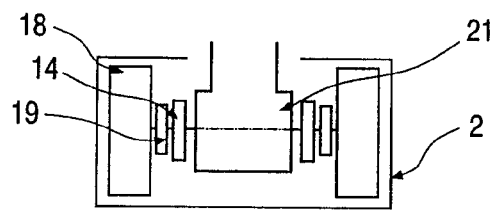
FIG. 6 is a diagrammatic cross-sectional view, taken at the area of the bearing with the bearing block of FIG. 5 in FIG. 1.
Figure 7:
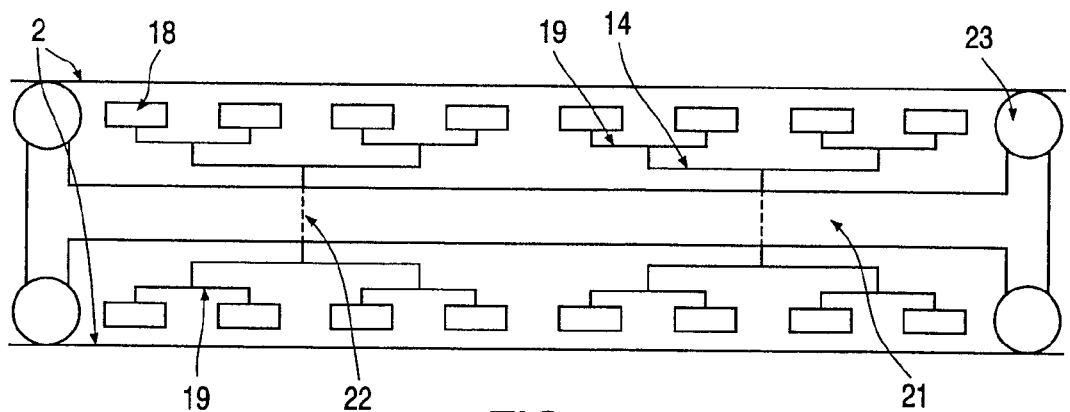
FIG. 7 is a diagrammatic longitudinal sectional view from above of the bearing of FIG. 6.

The FIGS. 6 and 7 illustrate the differences relative to the first preferred embodiment. FIG. 6 is a diagrammatic cross-sectional view of the C-arm 2 at the area of the bearing with the bearing block 21. FIG. 7 is a longitudinal sectional view from above of the bearing block 21 that is shown in FIG. 6. The bearing block 21 in this alternative preferred embodiment is provided with each time one row of roller elements 18 on both sides. The roller elements of one row are interconnected in pairs by means of connection members 19. The connection members 19 of two neighboring pairs of roller elements 18 in one row are interconnected by way of a further connection member 14. Each of the two connection members 19 is connected to the further connection members 14 so as to be independently movable. Furthermore, each time four pairs of roller elements 18 are connected to a common rotary shaft 22. Each of the two further connection members 14 is mounted on the rotary shaft 22 so as to be independently movable. The rotary shafts 12 (see FIG. 4) and 22 follow the curvature of the bearing block 11 (see FIG. 4) or 21, respectively.

The distance between the roller elements 8, 18 of a row is the same as much as possible in practice.

The side roller elements 13, 23 run on further running surfaces (not shown) that are provided on the inner side of the C-arm 2. Such further running surfaces extend mainly perpendicularly to the running surfaces 15, 16. The shafts of the side roller elements 13, 23 extend mainly perpendicularly to the shafts 12, 22 of the roller elements 8, 18.

The above-mentioned independent movement of the (further) connection members 9 and 14, 19, respectively, takes place mainly in the plane of the C-arm 2.

As a result of this construction, the operation of the bearing in accordance with the invention is smooth and light in all circumstances, despite irregularities in the bearing surfaces and/or despite any deformation of the C-arm occurring. The forces that act during the adjustment of the C-arm can be uniformly distributed among all roller elements, so that these elements are loaded to the same extent as much as possible and hence the bearing block overall has a service life that is longer than that of the bearing block in conformity with the present state of the art. Consequently, it suffices to provide a single row of roller elements of adequately large diameter on both sides of the bearing block. This offers the advantage that the roller elements need not be adjusted. This is contrary to other embodiments that are known in this technical field in which, for example, two rows of roller elements are provided on both sides of the bearing block. Exact adjustment of the wheels of co-operating rows on one side of the bearing block is then of crucial importance for suitable operation.

It is to be noted that the invention is not restricted to the preferred embodiments shown and described above. Notably the number of sets of roller elements in one row and the number of interconnected roller elements per set can be chosen at random. Because of the uniform distribution of the load, it is expected that the number of wheels in one row can be reduced, for example, to six wheels in each row. The diameter of the wheels should be adapted to the relevant situation and can also be chosen at random.

Consequently, the invention in general covers any implementation that is within the scope of the appended claims, considered in conjunction with the foregoing description and the accompanying drawings.

What is claimed is:

1. A device that is provided with a C-arm (7) for the mounting of medical equipment (5; 6), which C-arm is attached to a carrier (4) so as to be adjustable along its circumference, said carrier being provided with a bearing block (11) that is provided with at least one row of roller elements (8) on both sides, the C-arm being constructed so as to be hollow and being provided on both sides with at least two oppositely situated internal running surfaces (15, 16) for the roller elements, characterized in that a number of the roller elements of one row is interconnected by way of a connection member (9).

2. A device as claimed in claim 1, in which the roller elements of one row are grouped in two or more sets of roller elements, each set of roller elements being interconnected by way of a connection member.

3. A device as claimed in claim 2, in which the roller elements of one row are interconnected in pairs by way of connection members.

4. A device as claimed in claim 2, in which oppositely situated sets of roller elements are connected in pairs to a common rotary shaft (12) on both sides of the bearing block.

5. A device as claimed in claim 2, in which the connection members of two neighboring sets of roller elements in one row are interconnected by way of a further connection member (14).

6. A device as claimed in claim 5, in which oppositely situated further connection members are connected in pairs to a common rotary shaft (22) on both sides of the bearing block.

7. A device as claimed in claim 1, in which each connection member is movable mainly in the plane of the C-arm.

8. A device as claimed in claim 1, in which the bearing block exhibits a curvature that corresponds to the curvature of the C-arm, the rotary shafts being provided along the curvature.

9. A device as claimed in claim 1, in which the bearing block is provided with a number of side roller elements (13; 23) whose rotary shafts extend mainly perpendicularly to the rotary shafts of the roller elements, and in which the C-arm is provided with a third running surface (2) for the side roller elements.

10. A bearing block as described as part of the device as claimed in claim 1.

* * * * *